United States Patent
Urushiya

(10) Patent No.: US 7,555,096 B2
(45) Date of Patent: Jun. 30, 2009

(54) X-RAY CT APPARATUS AND IMAGE-TAKING METHOD THEREFOR

(75) Inventor: Hiroyuki Urushiya, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 157 days.

(21) Appl. No.: 11/150,431

(22) Filed: Jun. 13, 2005

(65) Prior Publication Data

US 2005/0276375 A1     Dec. 15, 2005

(30) Foreign Application Priority Data

Jun. 15, 2004    (JP)    ............................ 2004-177405

(51) Int. Cl.
A61B 6/00    (2006.01)

(52) U.S. Cl. ........................................ 378/19; 378/207

(58) Field of Classification Search ............... 378/4, 378/15–19, 901
See application file for complete search history.

(56) References Cited

U.S. PATENT DOCUMENTS

| | | | | |
|---|---|---|---|---|
| 4,580,219 | A * | 4/1986 | Pelc et al. | 382/131 |
| 4,703,424 | A * | 10/1987 | Gullberg et al. | 378/14 |
| 4,812,983 | A * | 3/1989 | Gullberg et al. | 378/14 |
| 4,841,553 | A * | 6/1989 | Nagai | 378/19 |
| 4,852,132 | A * | 7/1989 | Namikawa | 378/19 |
| 4,891,829 | A * | 1/1990 | Deckman et al. | 378/4 |
| 5,056,020 | A * | 10/1991 | Feldman et al. | 378/6 |
| 5,214,578 | A * | 5/1993 | Cornuejols et al. | 378/207 |
| 5,432,339 | A * | 7/1995 | Gordon et al. | 250/231.13 |
| 5,673,300 | A * | 9/1997 | Reckwerdt et al. | 378/65 |
| 5,828,718 | A * | 10/1998 | Ruth et al. | 378/19 |
| 6,229,869 | B1 * | 5/2001 | Hu | 378/4 |
| 6,466,639 | B2 * | 10/2002 | Nukui et al. | 378/8 |
| 6,522,712 | B1 * | 2/2003 | Yavuz et al. | 378/4 |
| 7,061,533 | B1 | 6/2006 | Urushiya | 348/346 |
| 2005/0276371 | A1 | 12/2005 | Urushiya | 378/4 |
| 2006/0049358 | A1 | 3/2006 | Oumi et al. | 250/370.08 |

FOREIGN PATENT DOCUMENTS

JP    2002-336237    11/2002

OTHER PUBLICATIONS

Azvedo et al., Calculation of the Rotational Centers in Computed Tomography Sinograms, IEEE Transactions on Nuclear Science, vol. 37, No. 4, Aug. 1990, pp. 1525-1540.*

Gullberg et al., Reconstruction for fan beam with an angular-dependent displaced center-of-rotation, Technical Rports: Crawfor, Gullberg, and Tsui: Reconstruction for fan beam, Oct. 1987, pp. 67-71.*

(Continued)

*Primary Examiner*—Edward J Glick
*Assistant Examiner*—Alexander H Taningco
(74) *Attorney, Agent, or Firm*—Fitzpatrick, Cella, Harper & Scinto

(57) ABSTRACT

Time-series data over the range of a projection angle is created from a sinogram. Then, time-series data made up of opposite data corresponding to the time-series data over the range of a projection angle is created. Based on the amount of the error between the two types of time-series data, the amount of position deviation of a revolution axis is calculated.

2 Claims, 6 Drawing Sheets

OTHER PUBLICATIONS

Gullberg et al., Estimation of geometrical parameters for fan beam tomography, Phys. Med. Biol., vol. 32, No. 12, 1987, pp. 1581-1594.*

Gullberg et al., Reconstruction Algorithm for Fan Beam with a Displaced Center-of-Rotation, IEEE Transactions on Medical Imaging, vol. MI-5, No. 1, Mar. 1986, pp. 23-29.*

* cited by examiner

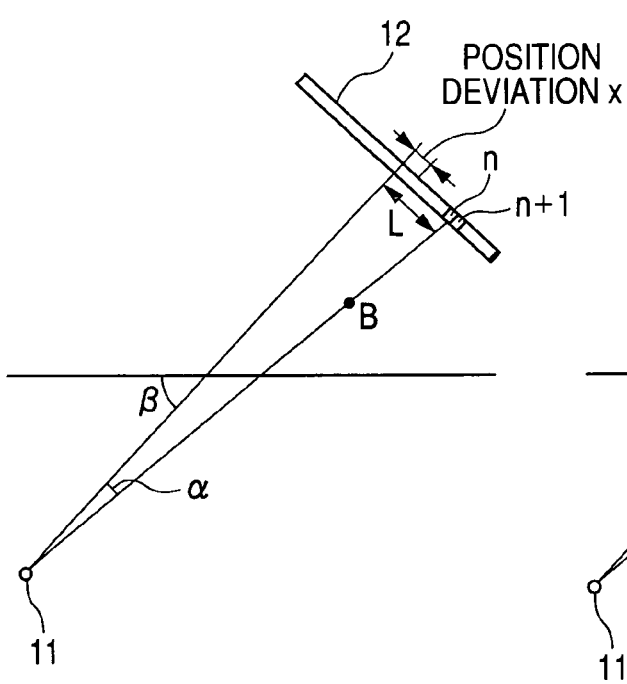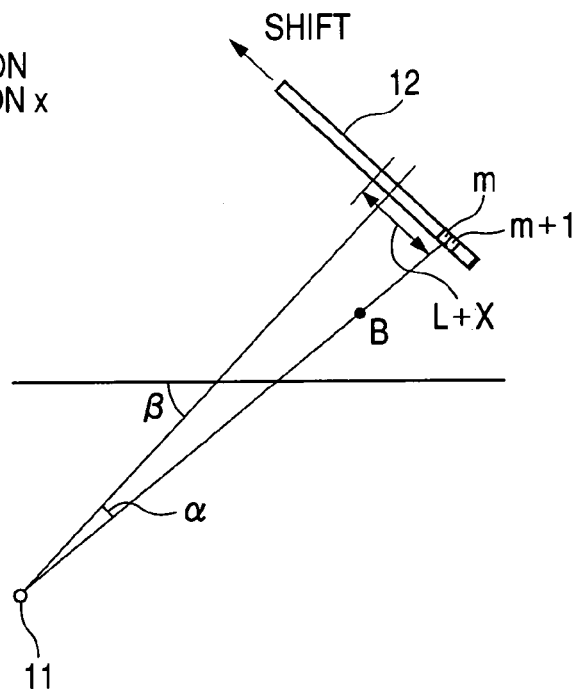

X-RAY CT APPARATUS AND IMAGE-TAKING METHOD THEREFOR

BACKGROUND OF THE INVENTION

1. Field of the Invention

The present invention relates to an X-ray CT apparatus for reconstructing tomographic images, by utilizing projection data.

2. Related Background Art

As illustrated in FIG. 4, in an X-ray CT (Computer Tomography) apparatus, an X-ray source 1 and an X-ray detector 2 are arranged so as to face each other, with a subject S being interposed between them; while the X-ray source 1 and the X-ray detector 2 or the subject S is are being revolved around a point within the subject S, each X-ray sequentially radiated by the X-ray source 1 is detected by the X-ray detector 2. By reconstructing and processing projection data created in this way, a tomographic image can be obtained. In this situation, the line that connects the X-ray source 1 with the center of the X-ray detector 2, i.e., the coordinate origin O for the projection data always passes through the revolution center point A.

However, if, due to mechanical misalignment, movement of the subject S, and the like, the line and the revolution center point A of the subject S deviate from each other, i.e. a condition changes from a state as illustrated in FIG. 5A to a state as illustrated in FIG. 5B, the coordinate origin of the projection data for the subject S is shifted. In FIGS. 5A and 5B, the case where the subject S rotates is illustrated; however, also in the case where the subject S is fixed, and where the X-ray source 1 and the X-ray detector revolve, the coordinate origin of the projection data for the subject S is shifted.

If the projection data whose coordinate system has been shifted in such a way is considered as if not shifted and is reconstructed as it is, an artifact or significant deterioration in an image may be caused. In order to detect such a position deviation of the revolution center point, for example, as disclosed in Japanese Patent Application Laid-Open No. 2002-336237, by taking images of a calibration phantom or a marker, the detection of a position deviation has conventionally been implemented.

However, when the position deviation of the revolution center point is detected by utilizing a calibration phantom, it is necessary to newly create a calibration phantom, and, further, it takes a time to collect data, while taking images of the phantom, whereby the efficiency is lowered. In addition, when a marker is used, it is necessary to newly create a marker; because the marker appears in a reconstructed tomographic image, diagnosis is hindered.

In the case where a fan beam is used as the X-ray source 1, as illustrated in FIG. 6, the X-ray transmission path with a fan angle α coincides with the X-ray transmission path with a fan angle −α and with a projection angle being turned by 180°+2α. It means that, supposing that the transmission data value of a transmission path with a fan angle α and a projection angle β is g(α, β), the transmission data value g(−α, β+π+2α) of the opposite transmission path coincides with g(α, β). That is to say, Equation (1) is yielded.

$$g(\alpha,\beta)=g(-\alpha,\beta+\pi+2\alpha) \quad (1)$$

Equation (1) is rendered as in FIG. 7, on a sinogram.

In contrast, in the case where the revolution center point A of the subject S is deviated, as described above, the deviation appears as a shift of projection data in the coordinate system; thus, the deviation is rendered as in FIG. 8, on a sinogram, and is expressed by Equation (2).

$$g(\alpha,\beta)=g(-\alpha+2x,\beta+\pi+2(\alpha-x)) \quad (2)$$

As described above, data that originally coincide appear on a sinogram, as expressed by Equation (1); however, in the case where a position deviation of the revolution center point A exists, data appear, as expressed by Equation (2).

SUMMARY OF THE INVENTION

The present invention has been implemented in consideration of the foregoing problems and provides a technology related to an X-ray CT apparatus that reduces an effect of a deviation of the revolution center point.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, an illustrate embodiment of the invention and, together with the description, serve to explain the principles of the invention.

FIGS. 3A and 3B are views for explaining correction through back projection, for a position deviation of a revolution center point;

FIG. 4 is a view for explaining geometrical relationships in an X-ray CT apparatus;

DESCRIPTION OF THE PREFERRED EMBODIMENTS

Figure 1:
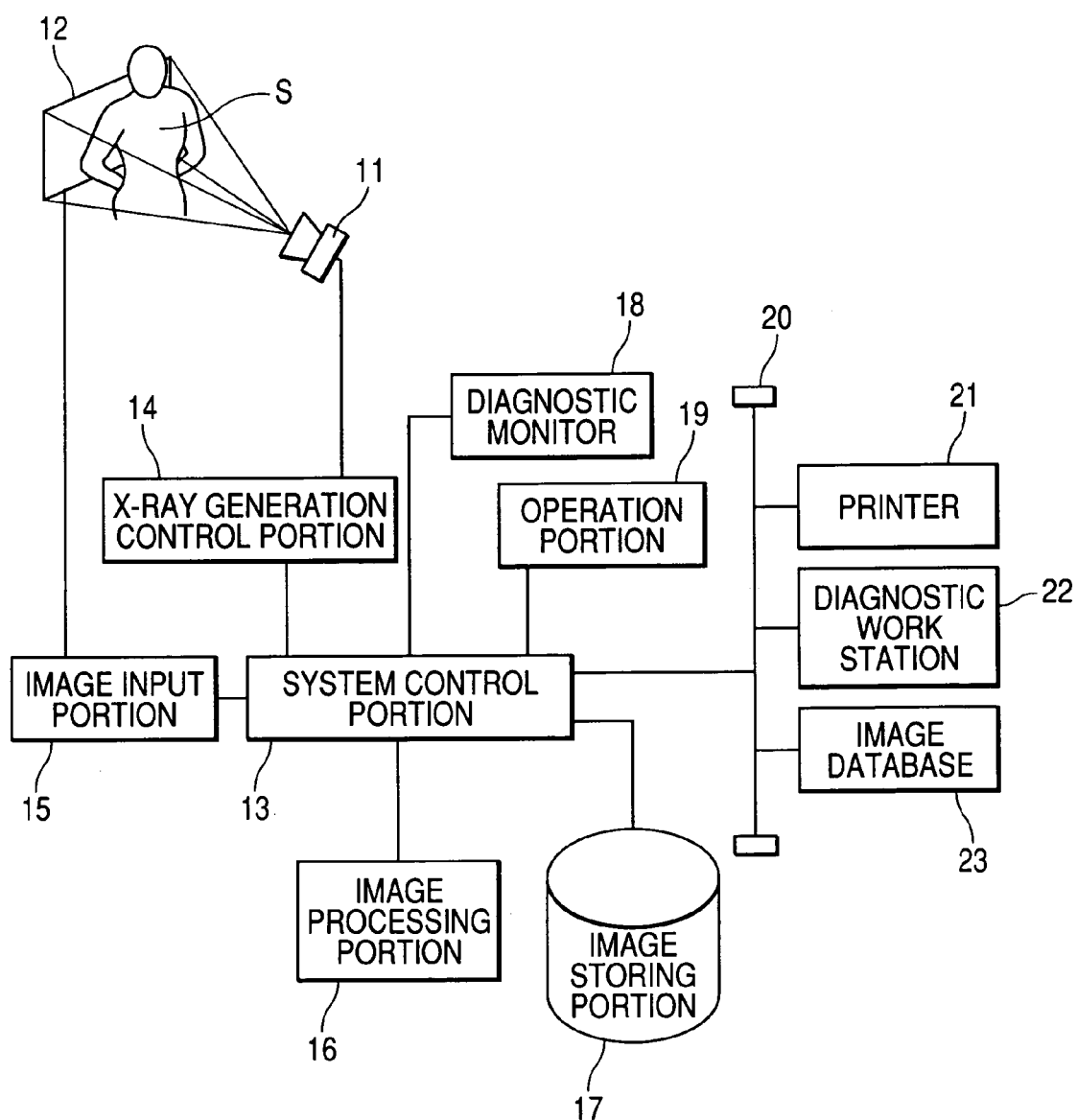
FIG. 1 is a block diagram of an X-ray CT system.

Preferred embodiment of the present invention will now be described in detail in accordance with the accompanying drawings.

The present invention will be explained in detail, based on an embodiment illustrated in the drawings.

Embodiment 1

FIG. 1 is a block diagram of an X-ray CT system. An X-ray source 11 and an X-ray detector 12 are arranged, with a subject S, which is a patient, being interposed between them; the output of an system control portion 13 is connected via an X-ray generation control portion 14 to the X-ray source 11. In addition, the output of the X-ray detector 12 is connected via an image inputting portion 15 to the system control portion 13. Moreover, an image processing portion 16, an image storing portion 17, a diagnosis monitor 18, an operation portion 19, and a network 20 are connected to the system control portion 13; a printer 21, a diagnosis workstation 22, and an image database 23 are connected to the network 20.

An X-ray generated in the X-ray source 11 controlled by the X-ray generation control portion 14 penetrates the subject S and then is detected by the X-ray detector 12; the detected X-ray is inputted as a projection image to the system control portion 13, via the image inputting portion 15. The X-ray source 11 and the X-ray detector 12 collect a projection image at each predetermined rotation angle, while revolving around the subject S as a revolution center. Alternatively, a subject fixed on a rotating table may be rotated, while the positional relationship between the X-ray source 11 and the X-ray detector 12 being maintained.

The image processing portion 16, via the system control portion 13, implements image processing, such as correction of the X-ray detector 12, preprocessing including logarithmic transformation, and reconstruction processing, on the inputted projection images collected at respective rotation angles, thereby creating tomographic images. The created tomographic images are displayed on the diagnosis monitor 18, stored in the image storing portion 17, and outputted via the network 20 to the printer 21, the diagnosis workstation 22, and the image database 23. Various types of processing, such as window operation of display, display-switching operation of tomographic images along the body axis, multi-planar reconstruction operation, and 3-D surface display operation, are implemented by the operation portion 19.

Figure 2:
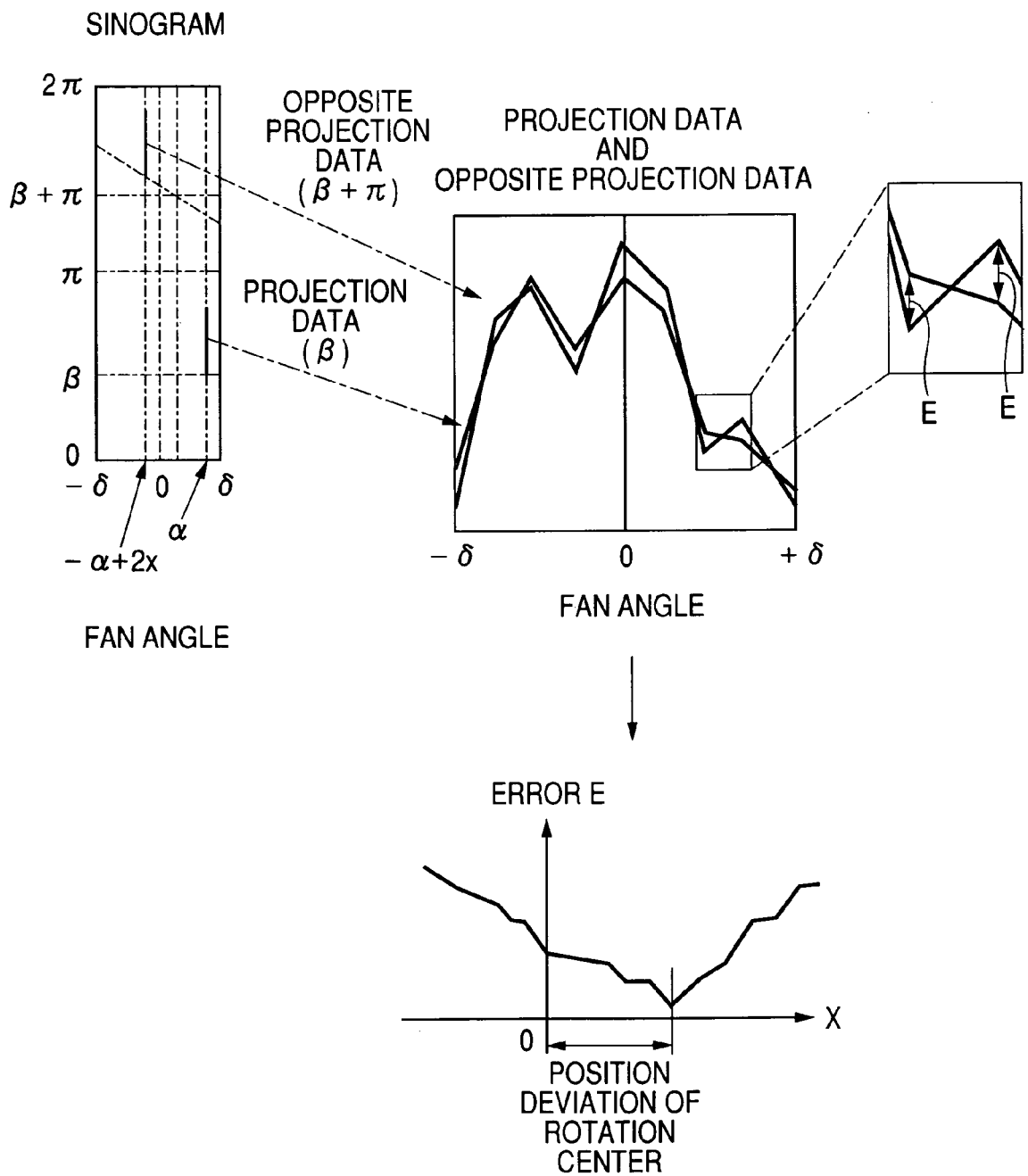
FIG. 2 is a diagram for explaining an operational example.
Figure 5A:
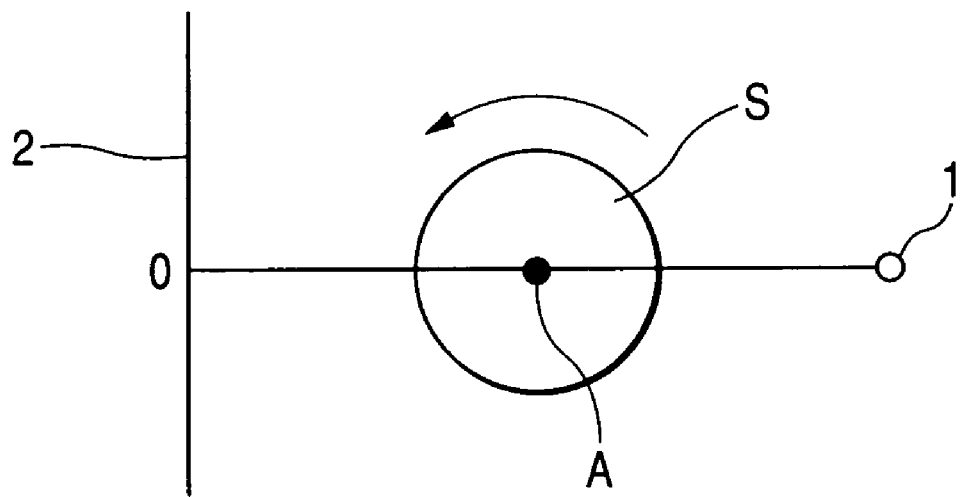
FIGS. 5A and 5B are views for explaining a position deviation of a revolution center point.
Figure 5B:
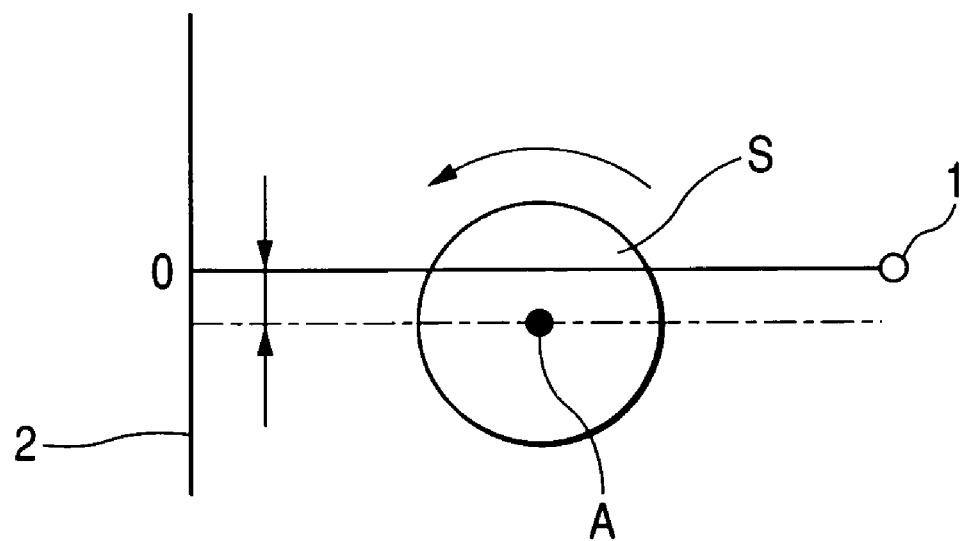

FIG. 2 is a diagram for explaining an operational example of the X-ray CT system. By creating, from a sinogram, time-series data over a projection angle range in a channel, by creating time-series data made up of opposite fan-beam projection data, while supposing that the position deviation x of the revolution center point exists, and by obtaining errors between these time-series data, the amount of a position deviation that makes the error minimal is defined as the position deviation of the revolution center point, in that image taking.

In order to implement this, Steps 1 to 6 below are carried out.

(1) Step 1: Creation of a Sinogram

Figure 6:
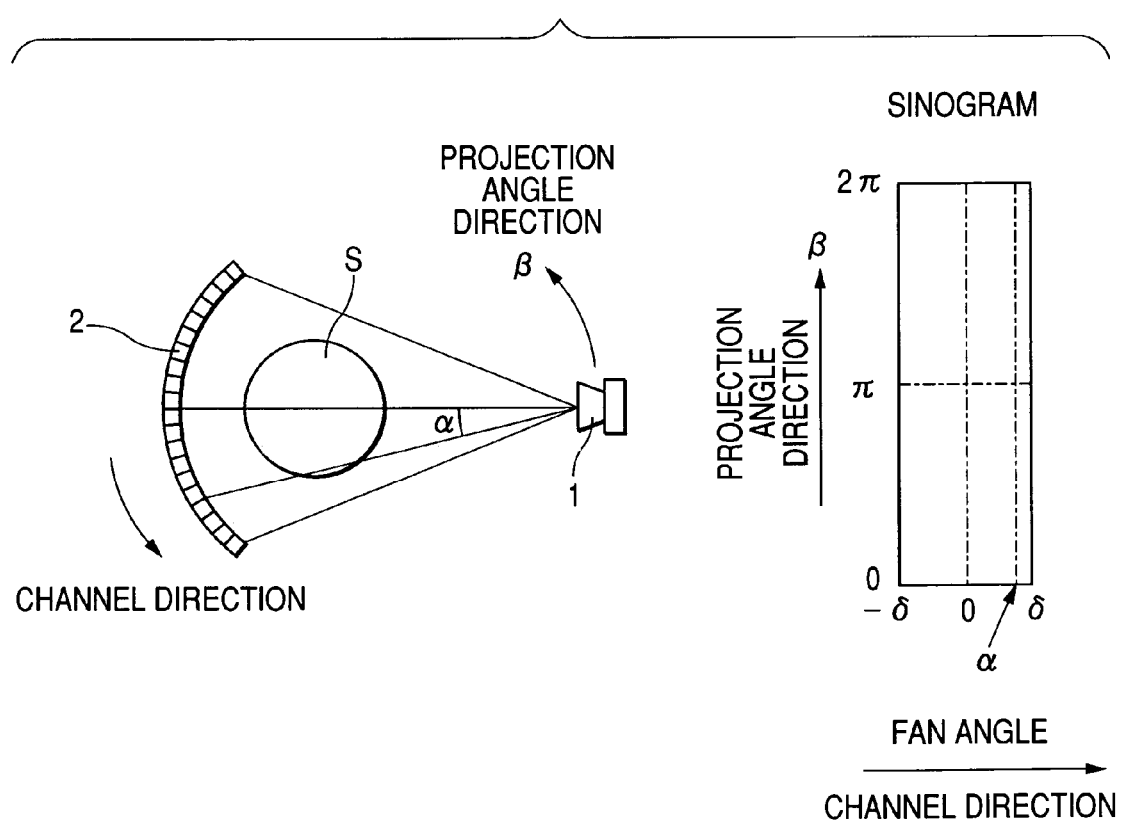
FIG. 6 includes views for explaining an X-ray projection angle and a sinogram.
Figure 7:
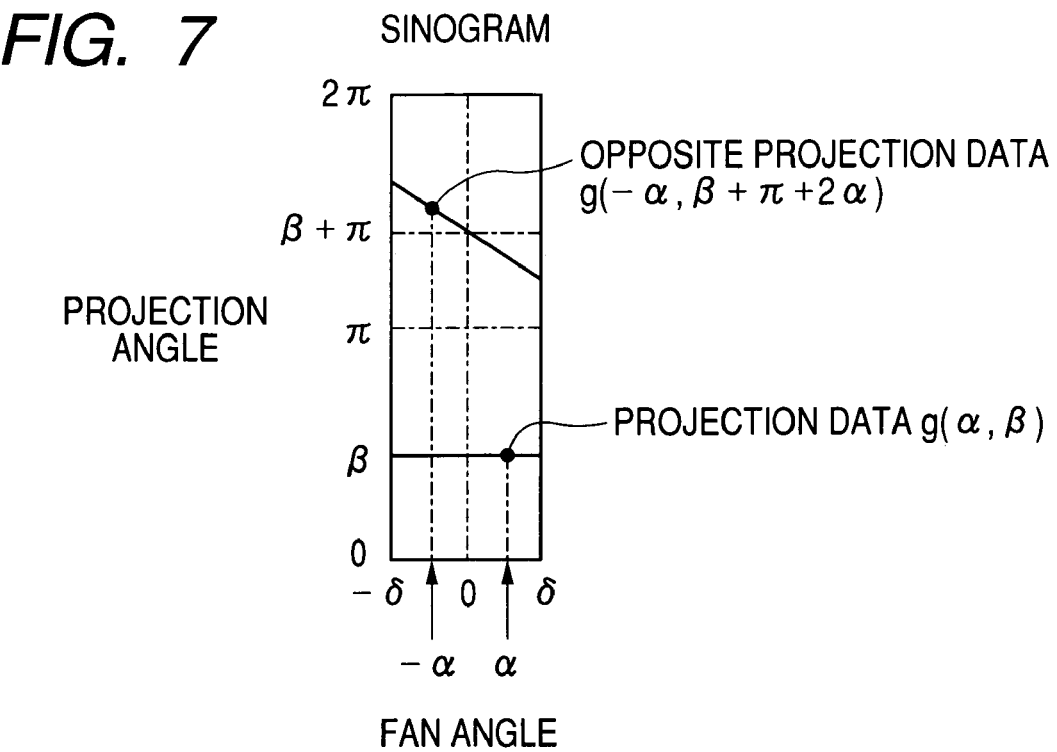
FIG. 7 is a diagram for explaining opposite projection data, through a sinogram.

A sinogram is, as illustrated in FIG. 6, an image made up of arranged projection data, with an abscissa indicating the channel direction (fan angle) of the X-ray detector 12 and with an ordinate indicating the direction of projection angle.

In the case where a two-dimension planar detector is utilized as the X-ray detector 12, a row of detectors situated at specific positions may be utilized along the body axis. The specific positions may be, for example, positions that are along the center axis of an X-ray beam. Alternatively, if it is possible that the amount of the position deviation of the revolution center point varies along the body axis, by obtaining, at a plurality of appropriate positions, deviations of the revolution center point, and by connecting these deviations through interpolation or fitting, the position deviations of the revolution center point, at an arbitrary position along the body axis, can be obtained.

(2) Step 2: Creation, from a Sinogram, of Time-Series Data Over a Projection Angle Range in a Channel By selecting an appropriate channel from a sinogram, e.g., in FIG. 2, by selecting a channel having a fan angle α, time-series data is created over an appropriate projection angle range β to β+γ of this channel. The selection of a channel is implemented in such a way that all X-rays that enter the channel have penetrated the subject S, and that the channel is not too close to the center.

If a calculation time should be shortened, the width γ of a projection angle range may be made short, and if the calculation time is not so important, the width may be made long.

Figure 8:
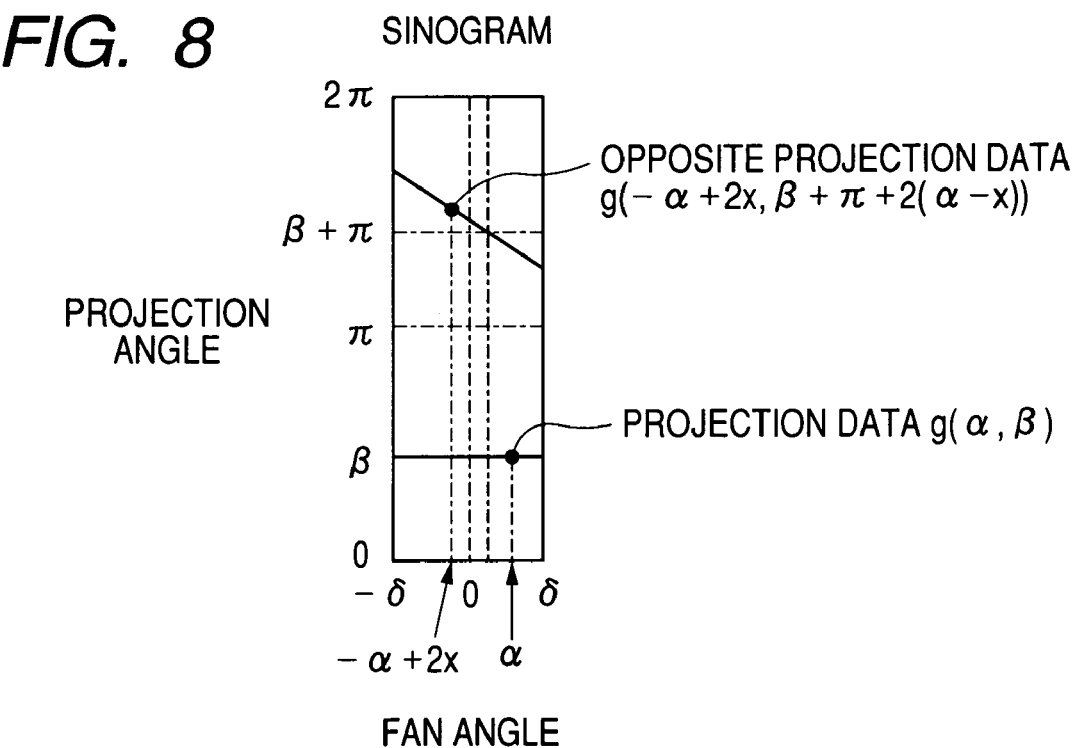
FIG. 8 is a diagram for explaining opposite projection data, through a sinogram, in the case where a position deviation of a revolution center point exists.

(3) Step 3: creation of Time-Series Data, Made Up of Opposite Data, Corresponding to Time-Series Data Over a Projection Angle Range, Created in Step 2, While Supposing that the Position Deviation x of the Revolution Center Point Exists As represented in FIG. 8, in the case where the position deviation x of the revolution center point exists, data corresponding to the deviation x appears on the sinogram, while being rendered as $g(\alpha, \beta)=g(-\alpha+2x, \beta+\pi+2(\alpha-x))$. By utilizing this, time-series data corresponding to the time-series data in Step 2 is created.

In other words, time-series data with regard to coordinates from $g(-\alpha+2x, \beta+\pi+2(\alpha-x))$ to $g(-\alpha+2x, \beta+\pi+2(\alpha-x)+\gamma)$ is created, corresponding to coordinates from $g(\alpha, \beta)$ to $g(\alpha, \beta+\gamma)$.

In this situation, for example, the projection data at the coordinates of fan angle $-\alpha+2x$ and the projection angle $\beta+\pi+2(\alpha-x)$ does not always exist; if no projection data exists at that coordinates, interpolation may be carried out by utilizing data at the coordinates before and after that coordinates.

(4) Step 4: Acquisition of the Amount of the Error Between the Time-Series Data in Step 2 and the Time-Series Data in Step 3

The time-series data in Step 2 and Step 3 can be rendered as one-dimension vector data for each projection angle $\beta_i$; such vectors are referred to as $g_i$ and $[g_i]$, respectively. The $g_i$ and $[g_i]$ should originally coincide with each other; the error between them is obtained as an evaluation amount. The error can be obtained by Equation (3), i.e., by mean squared error E.

$$E=\sqrt{\Sigma(g_i-[g_i])^2} \quad (3)$$

Of course, it is not always required to calculate the square root; an absolute error $E=\Sigma|g_i-[g_i]|$ may be employed. It is indicated that the smaller the error E is, the better the two types of time-series data coincide.

(5) Step 5: Alternate Repetition of Steps 3 and 4, While Moving Within a Predetermined Range the Position Deviation x of the Revolution Center Point After deciding the predetermined range in which the position deviation x of the revolution center point may occur, the position deviation x is changed sequentially within the range. The method of changing the position deviation x may be implementing within the predetermined range sampling with a predetermined sampling space or a predetermined number of samples.

(6) Step 6: Regarding the Position Deviation x in Which an Error Amount is Minimal in Step 5 as the Position Deviation of the Revolution Center Point, in the Image Taking After, in Step 5, sequentially changing within a predetermined range the position deviation x, and then obtaining error amounts, the position deviation x in which the obtained error amount is minimal is regarded as the position deviation of the revolution center point, in the image taking. In order to obtain the amount of the position deviation with higher accuracy, by changing again the position deviation, within the range from the one adjacent sampling point, of the position corresponding to the position deviation obtained as above, to the other adjacent sampling point, as the predetermined range in Step 5, the position deviation can be detected with higher accuracy.

As described above, the position deviation of the revolution center point can be detected; the methods of correcting the detected position deviation include correcting projection data and implementing correction at the time of back projection (reverse-projection calculation).

The method of correcting projection data provides the creation of new projection data, by deviating projection data by the amount of the detected position deviation. In the case where the position deviation is not an integer, the new projection data is created by means of interpolation.

FIGS. 3A and 3B illustrate the method of implementing correction at the time of back projection; at back projection, as illustrated in FIG. 3A, by obtaining channels n and n+1 of the X-ray detector 12 on a projection coordinates L with which the line that connects a reconstruction point B and the X-ray source 11 crosses, and by interpolating data for the two channels n and n+1, by means of the projection coordinates L, back-projection data is obtained and then is added to the reconstruction point B. The foregoing process is implemented for each projection angle β and each reconstruction point B.

In this situation, if the position deviation x of the revolution center point exists, the projection coordinates may be deviated by x to L+x, as illustrated in FIG. 3B. By obtaining channels m and m+1, of the X-ray detector 12, that corresponds to the coordinates L+x, and by interpolating data for the two channels m and m+1, by means of the projection coordinates L+x, the back-projection data is obtained; adding the back-projection data to the reconstruction point B enables to correct and reconstruct the position deviation of the revolution center point.

As discussed above, by obtaining the position deviation of the revolution center point, projection data is corrected, or back projection is implemented, by supposing, at the time of back projection for reconstruction, that the coordinate system for projection data is shifted. Accordingly, reconstruction processing free of the position deviation of a revolution center point is provided; in consequence, the tomographic image to be obtained can be a high-quality image in which an artifact and deterioration are suppressed to be minimal.

As described heretofore, the present invention can provide a technology related to an X-ray CT apparatus that reduces effects of deviation of the revolution center point.

As many apparently widely different embodiments of the present invention can be made without departing from the spirit and scope thereof, it is to be understood that the invention is not limited to the specific embodiment thereof except as defined in the appended claims.

This application claims priority from Japanese Patent Application No. 2004-177405 filed on Jun. 15, 2004, which is hereby incorporated by reference herein.

What is claimed is:

1. An X-ray image taking apparatus comprising:
    an X-ray source generating a fan beam of X-rays;
    an X-ray detecting apparatus having a plurality of channels and receiving the fan beam of X-rays;
    a rotating table on which a subject is mounted, for rotating the subject about a rotation center;
    a first storing unit which stores a first time-series value of penetrated data output for a fan angle α (alpha) from at least one of the plurality of channels, while the rotating table rotates through an angle γ (gamma);
    a second storing unit which stores other time-series values of penetrated data each of which is output from each of the plurality of channels, while the rotating table rotates through an angle γ (gamma) from a state at which the rotating table has rotated 180+2α degrees from a condition when the storage of the first time-series value of penetrated data is started;
    calculating means which calculates a difference between the first time-series value and the other time-series value of penetrated data output from each of the plurality of channels;
    channel selecting means which selects a channel outputting the other time series value corresponding to the least difference; and
    deviation providing means which provides as a position deviation between the rotation center of the rotating table and a center axis of the fan beam, half a difference between
        a position of the selected channel selected by the channel selecting means and
        a position of the channel outputting the first time-series value.

2. A method for detecting an amount of position deviation of a revolution center point on the basis of data obtained by rotating about the revolution center point, an X-ray source generating a fan beam of X-rays and an X-ray detecting apparatus having a plurality of channels and receiving the fan beam of X-rays, said method comprising the steps of:
    a first step of causing an X-ray source and an X-ray detecting apparatus to rotate about the revolution center point, with the X-ray source generating a fan beam of X-rays and the X-ray detecting apparatus having a plurality of channels and receiving the fan beam of X-rays:
    a second step of assuming a channel direction of the X-ray detecting apparatus as an abscissa, assuming a projection angle of the X-ray beam with respect to the revolution center point as an ordinate, and obtaining a sinogram on the basis of the output values of outputs from the respective channels;
    a third step of obtaining a first time-series data over a first predetermined projection angle range, from a first channel of the plurality of channels, on the basis of the sinogram obtained in the second step;
    a fourth step of obtaining a second time-series data corresponding to the first time-series data, over a second predetermined projection angle range, from a second channel opposite to the first channel while supposing that a position deviation x of the revolution center point exists;
    a fifth step of acquiring an amount of a difference between the first-time series data and the second time-series data;
    a sixth step of alternating the second step and third step while varying the position deviation x of the revolution center point in a predetermined range; and
    a seventh step of determining the position deviation x in a case that the difference obtained in the fifth step designates a minimal, as the deviation of revolution center position in a process of reconstructing a tomographic image, wherein
        1) the sixth step includes an operation that the predetermined range is sequentially limited, and the third step to the seventh step are repeated to determine the position deviation, and
        2) the predetermined range is set by including both adjacent side of a data area wherein the position deviation x in a case that the difference obtained in the sixth step designates the minimal is obtained, and
        3) when the determined position deviation is not an integer number, projection data used for reconstructing the tomographic image is interpolated so as to reformulate new projection data.

* * * * *